(12) United States Patent
Kilcullen

(10) Patent No.: US 6,436,371 B2
(45) Date of Patent: Aug. 20, 2002

(54) ORAL COMPOSITION

(75) Inventor: Neil Kilcullen, Bebington (GB)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 0 days.

(21) Appl. No.: 09/805,524

(22) Filed: Mar. 13, 2001

(30) Foreign Application Priority Data

Mar. 14, 2000 (EP) .............................................. 00302065

(51) Int. Cl.$^7$ .......................... A61K 7/16; A61K 31/19; A61K 7/24; A61K 31/00; A61K 31/60
(52) U.S. Cl. .............................. 424/49; 424/55; 424/54; 426/3; 426/650; 514/1; 514/159
(58) Field of Search .............................. 424/49, 55, 48, 424/54; 426/3, 650; 514/1, 159

(56) References Cited

U.S. PATENT DOCUMENTS 4,844,883 A    7/1989   Patel

FOREIGN PATENT DOCUMENTS

| WO | 93/04664 | 3/1993 |
| WO | 98/31242 | 7/1998 |
| WO | 00/10520 | 3/2000 |

*Primary Examiner*—Frederick Krass
*Assistant Examiner*—Clinton Ostrup
(74) *Attorney, Agent, or Firm*—Milton L. Honig

(57) ABSTRACT

Oral composition comprises a wintergreen flavor imparting ingredient and having an alkaline pH, wherein the wintergreen flavor imparting ingredient is 2'-hydroxypropiophenone.

9 Claims, No Drawings

ORAL COMPOSITION

BACKGROUND OF THE INVENTION

1. Field of the Invention

The present invention relates to an oral composition comprising 2'-hydroxypropiophenone.

2. The Related Art

One of the commonest flavours used in oral care formulations is mint. Further, there are many different flavour ingredients which effect several different minty flavours to the consumer, for example, peppermint oil, spearmint oil and wintergreen oil to name a few. Wintergreen oil is a particularly popular flavour material and is commonly used in oral care formulations, particularly toothpastes, all over the world.

The flavour molecules which are usually used to impart a wintergreen flavour to such oral compositions are only ever used in toothpastes which have a substantially neutral pH, for example, the paste marketed by the applicant under the brand name 'Close-up®'.

It is well known in toothpaste manufacture that the main ingredient in wintergreen flavour, methyl salicylate, is unstable in alkaline pH ranges.

This presents a problem since some of the more popular oral care compositions are at a substantially alkaline pH. For example, bicarbonate toothpastes are marketed by many of the oral care consumer products suppliers and are only ever made at substantially alkaline pH ranges. Further, where calcium carbonate is used as a polishing agent, for example, in the developing and emerging markets, the general pH of a formulation is also substantially alkaline, often as high as 10.

The prior art literature also refers to wintergreen oil as a flavour ingredient. WO 98/31242 (Wrigley) discloses the use of 2'-hydroxypropiophenone as a substitute for the major wintergreen ingredient methyl salicylate. However, no mention is made of the fact that 2'-hydroxypropiophenone can also be used to overcome the disadvantages of methyl salicylate as a wintergreen flavour ingredient where the pH is alkaline.

It is an object of the invention to provide an oral composition which is stable, has a wintergreen flavour and is at an alkaline pH.

SUMMARY OF THE INVENTION

Accordingly, the present invention provides an oral composition including a wintergreen flavour imparting ingredient and having an alkaline pH, wherein the wintergreen flavour imparting ingredient is 2'-hydroxypropiophenone.

2'-hydroxypropiophenone is commercially available from Sigma-Aldrich Company Ltd., The Old Brickyard, Gillingham, Dorset SP12 4XT, United Kingdom. A synthesis for the compound may be found in Org. Synth. 13, 90 (1933).

It is an essential feature of the invention that the pH of the composition is alkaline. By this is meant that it is not neutral, or substantially neutral, and ranges from about 7.5 to about 12.

In a particular embodiment the pH is greater than 7.5 and preferably above 8.5.

The oral composition according to the invention typically comprises from 0.0001 to 1% by weight 2'-hydroxypropiophenone, preferably from 0.001 to 0.75% and especially from 0.1 to 0.2% by weight.

In a further aspect, the invention relates to a method for imparting a wintergreen flavour to an oral composition of alkaline pH by incorporation into the composition 2'-hydroxypropiophenone.

DETAILED DESCRIPTON

The oral composition according to the invention typically comprises further ingredients which are common in the art, such as:

antimicrobial agents, e.g. Triclosan, chlorhexidine, copper-, zinc- and stannous salts such as zinc citrate, zinc sulphate, zinc glycinate, sodium zinc citrate and stannous pyrophosphate, sanguinarine extract, metronidazole, quaternary ammonium compounds, such as cetylpyridinium chloride; bis-guanides, such as chlorhexidine digluconate, hexetidine, octenidine, alexidine; and halogenated bisphenolic compounds, such as 2,2' methylenebis-(4-chloro-6-bromophenol);

anti-inflammatory agents such as ibuprofen, flurbiprofen, aspirin, indomethacin etc.;

anti-caries agents such as sodium- and stannous fluoride, aminefluorides, sodium monofluorophosphate, sodium trimeta phosphate and casein;

plaque buffers such as urea, calcium lactate, calcium glycerophosphate and strontium polyacrylates; vitamins such as Vitamins A, C and E;

plant extracts;

desensitising agents, e.g. potassium citrate, potassium chloride, potassium tartrate, potassium bicarbonate, potassium oxalate, potassium nitrate and strontium salts;

anti-calculus agents, e.g. alkali-metal pyrophosphates, hypophosphite-containing polymers, organic phosphonates and phosphocitrates etc.;

biomolecules, e.g. bacteriocins, antibodies, enzymes, etc.;

flavours, e.g. peppermint and spearmint oils;

other proteinaceous materials such as collagen;

preservatives; e.g. methyl paraben;

opacifying agents; e.g. titanium dioxide;

colouring agents; e.g. FD&C Blue No. 1, FD&C Yellow No. 5;

pH-adjusting agents; e.g. monosodium phosphate, trisodium phosphate, sodium hydroxide, sodium carbonate;

sweetening agents; e.g. sodium saccharin, aspartame;

pharmaceutically acceptable carriers, e.g. starch, sucrose, water or water/alcohol systems etc.;

surfactants, such as anionic, nonionic, cationic and zwitterionic or amphoteric surfactants;

particulate abrasive materials such as silicas, aluminas, calcium carbonates, dicalciumphosphates, calcium pyrophosphates, hydroxyapatites, trimetaphosphates, insoluble hexametaphosphates and so on, including agglomerated particulate abrasive materials, usually in amounts between 3 and 60% by weight of the oral care composition;

humectants such as glycerol, sorbitol, propyleneglycol, xylitol, lactitol etc.;

binders and thickeners such as sodium carboxymethylcellulose, xanthan gum, gum arabic etc. as well as synthetic polymers such as polyacrylates and carboxyvinyl polymers such as Carbopol®;

polymeric compounds which can enhance the delivery of active ingredients such as antimicrobial agents can also be included. Examples of such polymers are copolymers of polyvinylmethylether with maleic anhydride and other similar delivery enhancing polymers, e.g. those described in DE-A-3,942,643 (Colgate);

buffers and salts to buffer the pH and ionic strength of the oral care composition; and other optional ingredients that may be included are e.g. bleaching agents such as peroxy compounds e.g. potassium peroxydiphosphate, effervescing systems such as sodium bicarbonate/citric acid systems, colour change systems, and so on.

Liposomes may also be used to improve delivery or stability of active ingredients.

The oral compositions may be in any form common in the art, e.g. toothpaste, gel, mousse, aerosol, gum, lozenge, powder, cream, etc. and may also be formulated into systems for use in dual-compartment type dispensers.

Particular embodiments according to the invention are illustrated with the following non-limiting examples:

EXAMPLE 1

| | Percent by Weight |
|---|---|
| Calcium carbonate | 40.00 |
| Sorbitol | 27.00 |
| Hydrated silica | 2.00 |
| Sodium carboxymethyl cellulose | 0.90 |
| Sodium lauryl sulphate | 2.00 |
| Titanium dioxide | 1.00 |
| Sodium monofluorophosphate | 0.80 |
| Trisodium phosphate | 0.50 |
| Sodium saccharin | 0.20 |
| Flavour oil comprising 2'-hydroxypropiophenone | 1.20 |
| Water | 24.40 |
| pH = 9.7 | |

EXAMPLE 2

| | Percent by Weight |
|---|---|
| Hydrated silica | 18.50 |
| Sorbitol | 45.00 |
| Polyethylene glycol | 5.00 |
| Sodium carboxymethyl cellulose | 0.90 |
| Sodium lauryl sulphate | 1.50 |
| Titanium dioxide | 1.00 |
| Sodium bicarbonate | 5.00 |

-continued

| | Percent by Weight |
|---|---|
| Sodium fluoride | 0.22 |
| Sodium saccharin | 0.50 |
| Flavour oil comprising 2'-hydroxypropiophenone | 1.00 |
| Water | 21.38 |
| pH = 9.1 | |

What is claimed is:

1. Oral composition comprising a wintergreen flavour imparting ingredient and having an alkaline pH, characterised in that the wintergreen flavour imparting ingredient is 2'-hydroxypropiophenone.

2. Oral composition according to claim 1, wherein it has a pH greater than 7.5.

3. Oral composition according to claim 1, wherein it has a pH greater than 8.5.

4. Oral composition according to claim 1, wherein it comprises as a polishing agent calcium carbonate.

5. Oral composition according to claim 1, wherein it comprises sodium bicarbonate.

6. Oral composition of alkaline pH comprising 0.0001 to 1% by weight of the composition of 2'-hydroxypropiophenone as a wintergreen flavour imparting ingredient.

7. A method for imparting a wintergreen flavour to an oral composition of alkaline pH by incorporating into the composition 0.0001 to 1% by weight of the composition of 2'-hydroxypropiophenone.

8. Oral composition comprising:
   (i) an effective amount of methyl salicylate to impart a wintergreen flavour to the composition;
   (ii) from 0.0001 to 1% of 2'-hydroxypropiophenone by weight of the composition; and
wherein the composition has a pH ranging from about 7.5 to about 12.

9. Oral composition according to claim 8, wherein the pH is above 8.5.

* * * * *